(12) United States Patent
Hubin et al.

(10) Patent No.: US 6,656,450 B2
(45) Date of Patent: Dec. 2, 2003

(54) MACROCYCLIC MAGNETIC RESONANCE IMAGING CONTRAST AGENTS

(75) Inventors: Timothy J. Hubin, McPherson, KS (US); Thomas J. Meade, Altadena, CA (US)

(73) Assignee: California Institute of Technology, Inc., Pasadena, CA (US)

( * ) Notice: Subject to any disclaimer, the term of this patent is extended or adjusted under 35 U.S.C. 154(b) by 0 days.

(21) Appl. No.: 09/908,436

(22) Filed: Jul. 17, 2001

(65) Prior Publication Data

US 2002/0049308 A1 Apr. 25, 2002

Related U.S. Application Data

(60) Provisional application No. 60/218,581, filed on Jul. 17, 2000.

(51) Int. Cl.[7] .......................... A61B 5/055; C07D 255/02
(52) U.S. Cl. ..................................... 424/9.363; 540/474
(58) Field of Search ............................. 424/9.36, 9.361, 424/9.363, 1.65; 540/465, 474, 145; 534/10, 11, 12, 13

(56) References Cited

U.S. PATENT DOCUMENTS

| 3,919,102 A | 11/1975 | Kuhling et al. |
|---|---|---|
| 4,637,988 A | 1/1987 | Hinshaw et al. |
| 4,647,447 A | 3/1987 | Gries et al. |
| 4,678,667 A | 7/1987 | Meares et al. |
| 4,822,594 A | 4/1989 | Gibby |
| 4,837,169 A | 6/1989 | Toner |
| 4,877,872 A | 10/1989 | Morgan et al. |
| 4,885,363 A | 12/1989 | Tweedle et al. |
| 5,087,440 A | 2/1992 | Cacheris et al. |
| 5,095,099 A | 3/1992 | Parkinson et al. |
| 5,133,956 A | 7/1992 | Garlich et al. |
| 5,155,215 A | 10/1992 | Ranney |
| 5,188,816 A | 2/1993 | Sherry et al. |
| 5,219,553 A | 6/1993 | Kraft et al. |
| 5,230,883 A | 7/1993 | Kornguth et al. |
| 5,256,395 A | 10/1993 | Barbet et al. |
| 5,262,532 A | 11/1993 | Tweedle et al. |
| 5,292,414 A | 3/1994 | Sessler et al. |
| 5,310,539 A | 5/1994 | Williams |
| 5,322,681 A | 6/1994 | Klaveness |
| 5,332,567 A | 7/1994 | Goldenberg |
| 5,338,532 A | 8/1994 | Tomalia et al. |
| 5,358,704 A | 10/1994 | Desreux et al. |
| 5,407,657 A | 4/1995 | Unger et al. |
| 5,419,893 A | 5/1995 | Berg et al. |
| 5,446,145 A | 8/1995 | Love et al. |
| 5,466,438 A | 11/1995 | Unger et al. |
| 5,466,439 A | 11/1995 | Gibby et al. |
| 5,531,978 A | 7/1996 | Berg et al. |
| 5,554,748 A | 9/1996 | Sieving et al. |
| 5,565,552 A | 10/1996 | Magda et al. |
| 5,622,821 A | 4/1997 | Selvin et al. |
| 5,707,605 A | 1/1998 | Meade et al. |
| 5,874,573 A | * 2/1999 | Winchell et al. ............ 540/465 |
| 5,914,095 A | 6/1999 | Watson |
| 5,955,605 A | 9/1999 | Axworthy et al. |
| 5,980,862 A | 11/1999 | Meade et al. |

FOREIGN PATENT DOCUMENTS

| CA | 2197074 | 8/1994 |
|---|---|---|
| CA | 2139374 | 7/1995 |
| CA | 2182686 A1 | 8/1995 |
| WO | WO 90/12050 | 10/1990 |
| WO | WO 92/19264 | 11/1992 |
| WO | WO 94/03271 A1 | 2/1994 |
| WO | WO 94/04485 A1 | 3/1994 |
| WO | WO 95/10217 A2 | 4/1995 |
| WO | WO 95/19185 A1 | 7/1995 |
| WO | WO 95/19347 A1 | 7/1995 |
| WO | WO 95/20353 A1 | 8/1995 |
| WO | WO 95/27705 | 10/1995 |
| WO | WO 95/28966 | 11/1995 |
| WO | WO 95/31444 | 11/1995 |
| WO | WO 95/32741 | 12/1995 |
| WO | WO 96/23526 | 8/1996 |
| WO | WO 96/38184 | 12/1996 |
| WO | WO 97/01360 A3 | 1/1997 |
| WO | WO 97/21431 | 6/1997 |
| WO | WO 97/32862 | 9/1997 |
| WO | WO 97/36619 | 10/1997 |
| WO | WO 99/21592 | 5/1999 |
| WO | WO 99/59640 A2 | 11/1999 |
| WO | WO 01/08712 A2 | 2/2001 |
| WO | WO 01/52906 A2 | 7/2001 |

OTHER PUBLICATIONS

Aguayo, J.B., et al. "Nuclear Magnetic Resonance Imaging of a Single Cell," Nature, Letters to Nature 322:190–191 (Jul. 10, 1986).

Alexander, "Design and Synthesis of Macrocyclic Ligands and Their Complexes of Lanthanides and Antinides," Chem. Review, 95:273–342 (1995).

Borch, R.F., et al. "The Cyanohydridoborate Anion as a Selective Reducing Agent," Journal of the American Chemical Society 93(12): 2897–2904 (Jun. 16, 1971).

Cho, Z.H., et al. "Some Experiences on a 4μµm NMR Microscopy," Book of Abstracts, vol. 1, p. 233, Society of Magnetic Resonance in Medicine, 6th Annual Meeting and Exhibition, Aug. 17–21, 1987, New York City, NY.

Grynkiewicz, G., et al. "A New Generation of Ca2+ Indicators with Greatly Improved Fluorescence Properties," The Journal of Biological Chemistry, 260(6): 3440–3450 (1985).

Hennessy, M.J., et al. "NMR Surface Coil Microscopy," Book of Abstracts, vol. 2, p. 461–462, Society of Magnetic Resonance in Medicine, 5th Annual Meeting and Exhibition, Aug. 19–22, 1986, Montreal, Quebec, Canada.

(List continued on next page.)

*Primary Examiner*—Michael G. Hartley
(74) *Attorney, Agent, or Firm*—Dorsey & Whitney LLP; Robin M. Silva; Renee M. Kosslak

(57) ABSTRACT

The invention relates to novel magnetic resonance imaging contrast agents.

10 Claims, 3 Drawing Sheets

OTHER PUBLICATIONS

Hoult, D.I., et al. "The Signal–to–Noise Ratio of the Nuclear Magnetic Resonance Experiment," Journal of Magnetic Resonance, 24: 71–85 (1976).

Jackels, "Section III: Enhancement Agents for Magnetic Resonance and Ultrasound Imaging. Chapter 20: Enhancement Agents for Magnetic Resonance Imaging: Fundamentals," Pharm. Med. Imag. Section III, Chap 20, pp. 645–661 (1990).

Jacobs and Fraser, "Magnetic Resonance Microscopy of Embryonic Cell Lineages and Movements," Science, 263:681–684 (1994).

Johnson, G.A., et al., "MR Microscopy at 7.0 T," Works in Progress, Society of Magnetic Resonance in Medicine, Sixth Annual Meeting and Exhibition, Aug. 17–21, 1987, New York City, NY. p. 23.

Li, et al., "A Calcium–Sensitive Magnetic Resonance Imaging Contrast Agent," J. Am. Chem. Soc., 121:1413–1414 (1999).

Meade, T.J. et al., "Hydrophobic, Regiospecific Guest Binding by Transition–Metal Host Complexes Having Permanent Voids as Revealed by FT–NMR Relaxation Studies," J. Am. Chem. Soc., 108:1954–1962 (1986).

Meyer et al., "Advances in Macrocyclic Gadolinium Complexes as Magnetic Resonance Imaging Contrast Agents," Investigative Radiology, 25(1):S53–S55 (Sep. 1990).

Moats, et al., "A "Smart" Magnetic Resonance Imaging Agent That Reports on Specific Enzymatic Activity," Angew. Chem. Int. Ed. Engl., 36(7): 726–728 (Apr. 1997).

Moi, M.K., et al. "The Peptide Way to Macrocyclic Bifunctional Chelating Agents: Synthesis of 2–(p–Nitrobenzyl) –1,4,7,10–tetraazacyclododecan– N, N, N, N—tetraacetic Acid and Study of Its Yttrium (III) Complex," J. Am. Chem. Soc. 110(18):6266–6267 (1988).

Nijhof, E.J., et al. "High–Resolution Proton Imaging at 4.7 Tesla," Proceedings of Soc. Magn. Reson. Med., p. 925 (1987).

Runge, V.M., et al. "Future Directions in Magnetic Resonance Contrast Media," Top Magn. Reson. Imaging., 3(2):85–97 (1991).

Russell, E.J., et al. "Multicenter Double–Blind Placebo–Controlled Study of Gadopentetate Dimeglumine as an MR Contrast Agent: Evaluation in Patients with Cerebral Lesions," American Journal of Roentgenology, 152:813–823 (Apr. 1989).

Shukla, et al., "Design of Conformationally Rigid Dimeric MRI Agents," Magnetic Resoance in Medicine, 36(6): 928–931 (1996).

Sillerud, L.O., et al. "Proton NMR Microscopy of Intact Multicellular Tumor Spheroids," Book of Abstracts, vol. 1, p. 468, Society of Magnetic Resonance in Medicine, 6th Annual Meeting and Exhibition, Aug. 17–21, 1987, New York City, NY.

Staubli and Meade, "The Design and Synthesis of Fluorescently Detectable Magnetic Resonance imaging Agents for Embryonic Cell Lineage Analysis," American Chemical Society: Division of Inorganic Chemistry, 209th ACS National Meeting, Anaheim, California. Abstract No. 385 (Apr. 2–6, 1995).

Tsien, R.Y. "New Calcium Indicators and Buffers with High Selectivity Against Magnesium and Protons: Design, Synthesis, and Properties of Prototype Structures," Biochemistry, 19(11): 2396–2404 (1980).

Tweedle, M.F., et al. "Considerations Involving Paramagnetic Coordination Compounds as Useful NMR Contrast Agents," Nucl. Med. Bio. 15(1):31–36 (1988).

Hubin et al., "Potentiometric Titrations and Nickel (II) Complexes of Four Topologically Constrained Tetraazamacrocycles," Supramolecular Chemistry, 13:261–276 (2001).

Hubin et al., "Topologically Constrained Mangfanese (III) and Iron (III) Complexes of Two Cross–Bridged Tetraazamacrocycles," Inorg. Chem. 40;435–444 (2001).

Wong et al, "Synthesis and Charaterciaztion of Cross–Briged Cyclams and Pendant–Armed Derivatives and Structural Studies of Their Copper (II) Complexes," J. Am. Chem. Soc. 122:10561–10572 (2000).

Hubin et al., "New Iron (II) and Manganese (II) Compleses of Two Ultra–Rigid, Cross–Briged Tetraazamacrocycles for Catalysis and Biomimicry," J. Am. Chem. Soc. 122:2515–2522 (2000).

Hubin et al., "Crystallographic Characterization of Stepwise Changes in LIgand Conformations as Thier Internal Topology cvhanges and Two Novel Cross–Bridged Tetraazamacrocyclic Copper (II) Complexes," Inorg. Chem. 38:4435–4446 (1999).

Hubin et al., "Ultra rigid cross–bridged tetraaazamacrocycles as ligands– the challenge and the solution," Chem. Commun., 1675–1676 (1998).

Weisman et al., "Synthesis and tranxition–metal complexes of new cross–bridges tetraamine ligands," Chem. Commun., 947–948 (1996).

Weisman et al., "Cross–Bridged Cyclam. Protonation an $Li^+$Complexation in a Diamond–Lattice Cleft," J. Am. Chem. Soc. 112:8604–8605 (1990).

* cited by examiner

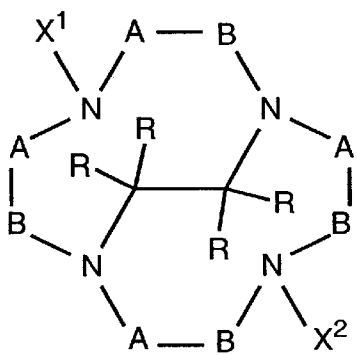
FIG._1A
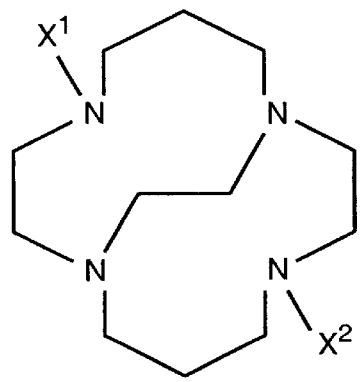
FIG._1B
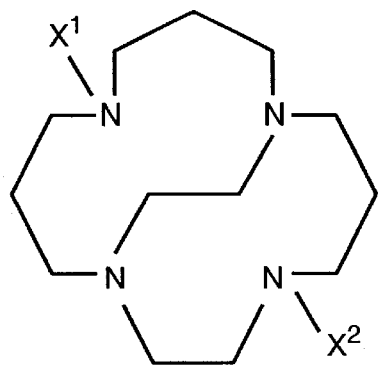
FIG._1C
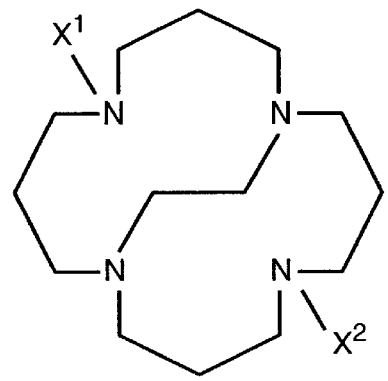
FIG._1D
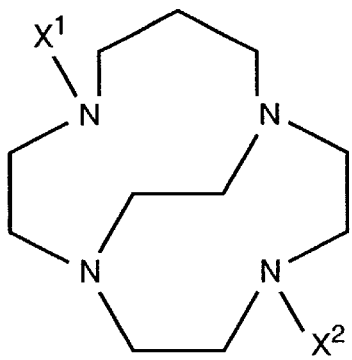
FIG._1E

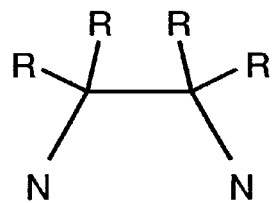
*FIG._2A*
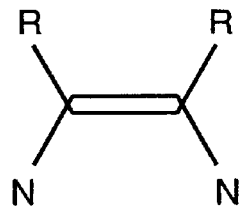
*FIG._2B*
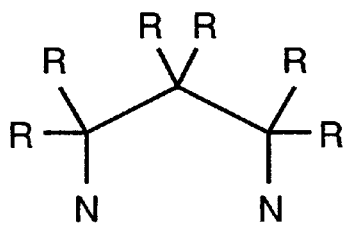
*FIG._2C*
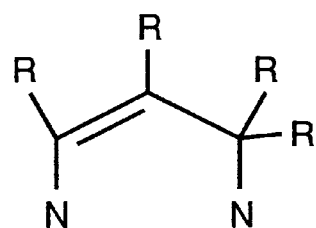
*FIG._2D*
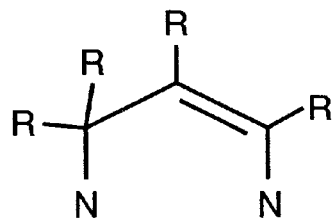
*FIG._2E*

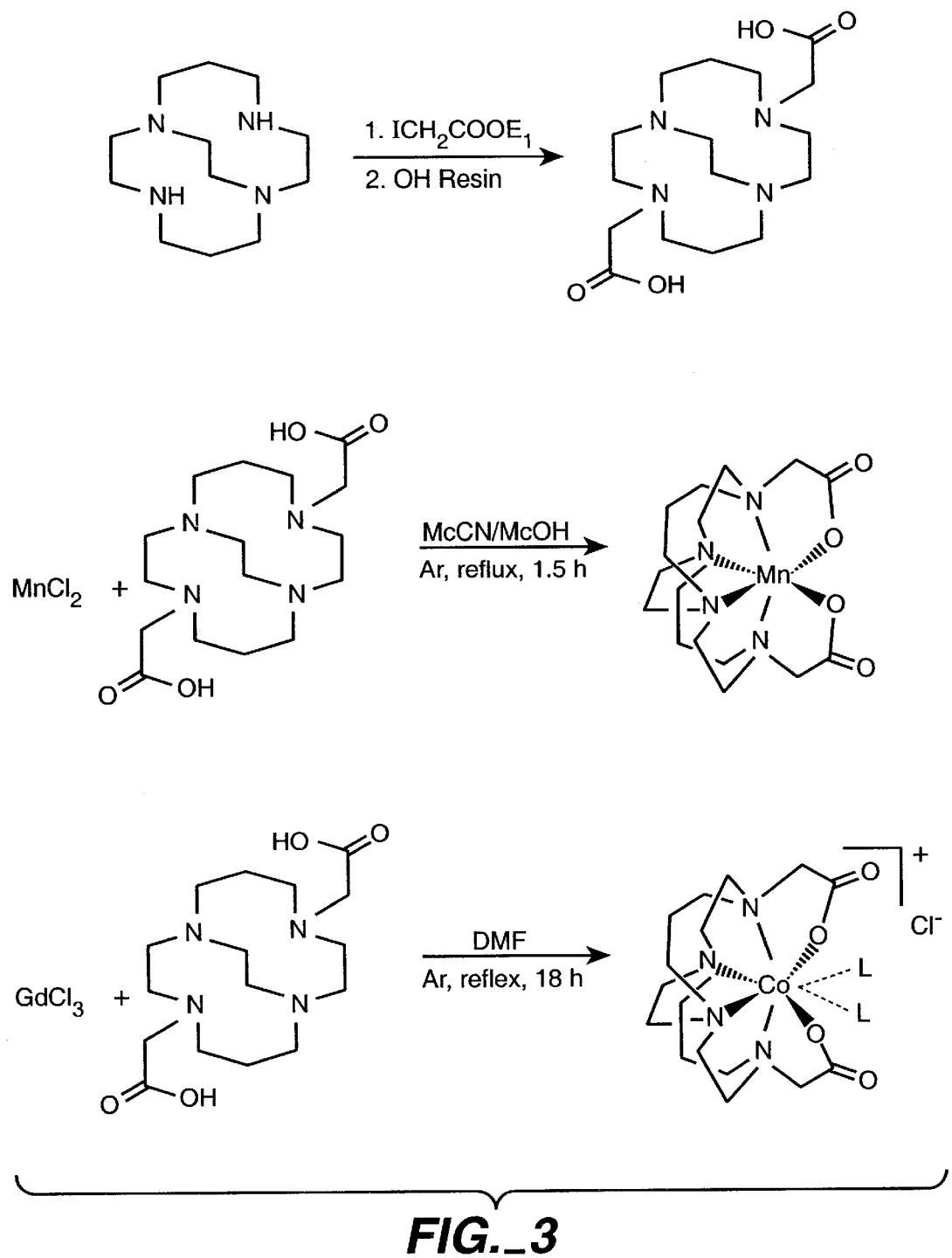
FIG._3

MACROCYCLIC MAGNETIC RESONANCE IMAGING CONTRAST AGENTS

This is a continuing application of U.S. Ser. No. 60/218,581, filed Jul. 17, 2000.

The U.S. government has certain rights in this invention pursuant to Grant No. RO 1AI47003 awarded by the National Institute of Health.

FIELD OF THE INVENTION

The invention relates to novel magnetic resonance imaging contrast agents.

BACKGROUND OF THE INVENTION

Magnetic resonance imaging (MRI) is a diagnostic and research procedure that uses high magnetic fields and radio-frequency signals to produce images. The most abundant molecular species in biological tissues is water. It is the quantum mechanical "spin" of the water proton nuclei that ultimately gives rise to the signal in all imaging experiments. In MRI the sample to be imaged is placed in a strong static magnetic field (1–12 Tesla) and the spins are excited with a pulse of radio frequency (RF) radiation to produce a net magnetization in the sample. Various magnetic field gradients and other RF pulses then act on the spins to code spatial information into the recorded signals. MRI is able to generate structural information in three dimensions in relatively short time spans.

The Image.

MR images are typically displayed on a gray scale with black the lowest and white the highest measured intensity (I). This measured intensity I=C*M, where C is the concentration of spins (in this case, water concentration) and M is a measure of the magnetization present at time of the measurement. Although variations in water concentration (C) can give rise to contrast in MR images, it is the strong dependence of the rate of change of M on local environment that is the source of image intensity variation in MRI. Two characteristic relaxation times, $T_1$ & $T_2$, govern the rate at which the magnetization can be accurately measured. $T_1$ is the exponential time constant for the spins to decay back to equilibrium after being perturbed by the RF pulse. In order to increase the signal-to-noise ratio (SNR) a typical MR imaging scan (RF & gradient pulse sequence and data acquisition) is repeated at a constant rate for a predetermined number of times and the data averaged. The signal amplitude recorded for any given scan is proportional to the number of spins that have decayed back to equilibrium since the previous scan. Thus, regions with rapidly decaying spins (i.e. short $T_1$ values) will recover all of their signal amplitude between successive scans.

The measured intensities in the final image will accurately reflect the spin density (i.e. water content). Regions with long $T_1$ values compared to the time between scans will progressively lose signal until a steady state condition is reached and will appear as darker regions in the final image. Changes in $T_2$ (spin-spin relaxation time) result in changes in the signal linewidth (shorter $T_2$ values) yielding larger linewidths. In extreme situations the linewidth can be so large that the signal is indistinguishable from background noise. In clinical imaging, water relaxation characteristics vary from tissue to tissue, providing the contrast which allows the discrimination of tissue types. Moreover, the MRI experiment can be setup so that regions of the sample with short $T_1$ values and/or long $T_2$ values are preferentially enhanced so called $T_1$-weighted and $T_2$-weighted imaging protocol.

MRI Contrast Agents.

There is a rapidly growing body of literature demonstrating the clinical effectiveness of paramagnetic contrast agents (currently 8 are in clinical trials or in use). The capacity to differentiate regions/tissues that may be magnetically similar but histologically distinct is a major impetus for the preparation of these agents [1, 2]. In the design of MRI agents, strict attention must be given to a variety of properties that will ultimately effect the physiological outcome apart from the ability to provide contrast enhancement [3]. Two fundamental properties that must be considered are biocompatability and proton relaxation enhancement. Biocompatability is influenced by several factors including toxicity, stability (thermodynamic and kinetic), pharmacokinetics and biodistribution. Proton relaxation enhancement (or relaxivity) is chiefly governed by the choice of metal and rotational correlation times.

The first feature to be considered during the design stage is the selection of the metal atom, which will dominate the measured relaxivity of the complex. Paramagnetic metal ions, as a result of their unpaired electrons, act as potent relaxation enhancement agents. They decrease the $T_1$ and $T_2$ relaxation times of nearby ($r^6$ dependence) spins. Some paramagnetic ions decrease the $T_1$ without causing substantial linebroadening (e.g. gadolinium (III), ($Gd^{3+}$)), while others induce drastic linebroadening (e.g. superparamagnetic iron oxide). The mechanism of $T_1$ relaxation is generally a through space dipole-dipole interaction between the unpaired electrons of the paramagnet (the metal atom with an unpaired electron) and bulk water molecules (water molecules that are not "bound" to the metal atom) that are in fast exchange with water molecules in the metal's inner coordination sphere (are bound to the metal atom).

For example, regions associated with a $Gd^{3+}$ ion (near-by water molecules) appear bright in an MR image where the normal aqueous solution appears as dark background if the time between successive scans in the experiment is short (i.e. $T_1$ weighted image). Localized $T_2$ shortening caused by superparamagnetic particles is believed to be due to the local magnetic field inhomogeneities associated with the large magnetic moments of these particles. Regions associated with a superparamagnetic iron oxide particle appear dark in an MR image where the normal aqueous solution appears as high intensity background if the echo time (TE) in the spin-echo pulse sequence experiment is long (i.e. $T_2$-weighted image). The lanthanide atom $Gd^{3+}$ is by the far the most frequently chosen metal atom for MRI contrast agents because it has a very high magnetic moment ($u^2$= 63$BM^2$), and a symmetric electronic ground state, ($S^8$). Transition metals such as high spin Mn(II) and Fe(III) are also candidates due to their high magnetic moments.

Once the appropriate metal has been selected, a suitable ligand or chelate must be found to render the complex nontoxic. The term chelator is derived from the Greek word chele which means a "crabs claw", an appropriate description for a material that uses its many "arms" to grab and hold on to a metal atom (see DTPA below). Several factors influence the stability of chelate complexes include enthalpy and entropy effects (e.g. number, charge and basicity of coordinating groups, ligand field and conformational effects). Various molecular design features of the ligand can be directly correlated with physiological results. For example, the presence of a single methyl group on a given ligand structure can have a pronounced effect on clearance rate. While the addition of a bromine group can force a given complex from a purely extracellular role to an effective agent that collects in hepatocytes.

Diethylenetriaminepentaacetic (DTPA) chelates and thus acts to detoxify lanthanide ions. The stability constant (K) for $Gd(DTPA)^{2-}$ is very high (logK=22.4) and is more commonly known as the formation constant (the higher the logK, the more stable the complex). This thermodynamic parameter indicates the fraction of $Gd^{3+}$ ions that are in the unbound state will be quite small and should not be confused with the rate (kinetic stability) at which the loss of metal occurs ($k_f/k_d$). The water soluble $Gd(DTPA)^{2-}$ chelate is stable, nontoxic, and one of the most widely used contrast enhancement agents in experimental and clinical imaging research. It was approved for clinical use in adult patients in June of 1988. It is an extracellular agent that accumulates in tissue by perfusion dominated processes.

To date, a number of chelators have been used, including diethylenetriaminepentaacetic (DTPA), 1,4,7,10-tetraazacyclododecane'-N,N'N",N'''-tetracetic acid (DOTA), and derivatives thereof. See U.S. Pat. Nos. 5,155,215, 5,087,440, 5,219,553, 5,188,816, 4,885,363, 5,358,704, 5,262,532, and Meyer et al., Invest. Radiol. 25: S53 (1990).

Image enhancement improvements using Gd(DTPA) are well documented in a number of applications (Runge et al., Magn, Reson. Imag. 3:85 (1991); Russell et al., AJR 152:813 (1989); Meyer et al., Invest. Radiol. 25:S53 (1990)) including visualizing blood-brain barrier disruptions caused by space occupying lesions and detection of abnormal vascularity. It has recently been applied to the functional mapping of the human visual cortex by defining regional cerebral hemodynamics (Belliveau 35 et al., (1991) 254:719).

Another chelator used in Gd contrast agents is the macrocyclic ligand 1,4,7,10-tetraazacyclododecane-N,N',N"N'''-tetracetic acid (DOTA). The Gd-DOTA complex has been thoroughly studied in laboratory tests involving animals and humans. The complex is conformationally rigid, has an extremely high formation constant (logk=28.5), and at physiological pH possess very slow dissociation kinetics. Recently, the GdDOTA complex was approved as an MRI contrast agent for use in adults and infants in France and has been administered to over 4500 patients.

Accordingly, it is an object of the invention to provide further examples of DOTA derivatives for use in MRI imaging.

SUMMARY OF THE INVENTION

In accordance with the objects outlined above, the present invention provides chelates having the formula:

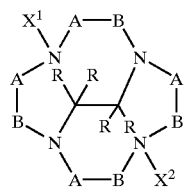

wherein
A—B is a structure selected from the group consisting of —$CR_2$—$CR_2$—, —CR=CR—, —$CR_2$—$CR_2$—$CR_2$—, CR=CR—$CR_2$— and —$CR_2$—CR=CR—;
$X^1$ and $X^2$ are independently selected from the group consisting of $CR_2$ $COO^-$, $^{CR}{}_2COOH$, $CR(CR_2COO^-)_2$, $CR(CR_2COOH)_2$;
each R is independently selected from the group consisting of hydrogen, alkyl, aryl, alcohol, amine, amido, nitro, ether, ester, ketone, imino, aldehyde, alkoxy, carbonyl, halogen, sulfur containing moiety, phosphorus containing moiety, targeting moiety, moiety, or, together with an adjacent R group forms an alkyl or aryl group.

In an additional aspect, the invention provides chelates having the formula:

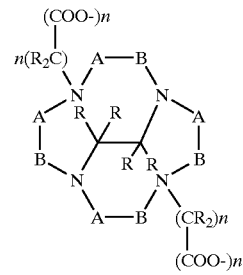

wherein each n is an integer independently selected from one to three.

In a further aspect, the invention provides compositions comprising a chelate of the invention complexed with a paramagnetic ion such as gadolinium, manganese or iron.

In an additional aspect, the invention provides compositions having the formula:

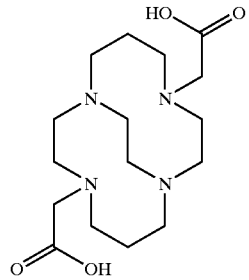

In a further aspect, the invention provides compositions having the formula:

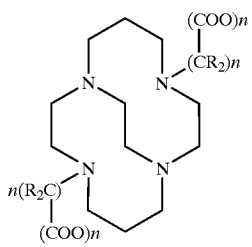

wherein each n is an integer independently selected from 1 to 3.

In an additional aspect, the invention provides chelates having the formula:

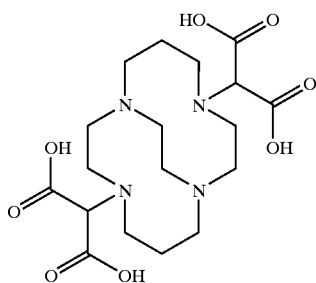

In a further aspect, the invention provides methods of magnetic resonance imaging of a cell, tissue or patient comprising administering an MRI agent of the invention to a cell, tissue or patient and rendering a magnetic resonance image of said cell, tissue or patient.

BRIEF DESCRIPTION OF THE DRAWINGS

FIGS. 1A–1E depict a variety of preferred embodiments utilizing macrocycles with four coordination atoms in the macrocycle. FIG. 1A depicts Structure 1 of the invention. FIGS. 1B–1E depict a variety of chelators of the invention, without the metal ions.

FIGS. 2A–2E depict a variety of suitable —A—B— groups, any one of which can be included in the macrocycles of the invention.

FIG. 3 depicts the synthetic schemes of the invention.

DETAILED DESCRIPTION OF THE INVENTION

The present invention provides novel magnetic resonance imaging contrast agents based on the DOTA structure, which can provide better and more stable MRI contrast agents. Cross-bridged tetraazamacrocycles have been shown to form complexes with transition metal ions having unprecedented kinetic stability, even though they do not fully saturate the metal's coordination sites. See Hubin et al., J. Chem. Soc. Chem, Commun, 1998:1675; Hubin et al., Inorg. Chem, 1999, 38:4435; Hubin et al., J. Am. Chem. Soc. 2000,122:2512; WO 98/39098 and WO 98/39046, all of which are expressly incorporated by reference.

The complexes of the invention comprise a chelator and a paramagnetic metal ion bound to the chelator. By "paramagnetic metal ion", "paramagnetic ion" or "metal ion" herein is meant a metal ion which is magnetized parallel or antiparallel to a magnetic field to an extent proportional to the field.

Generally, these are metal ions which have unpaired electrons; this is a term understood in the art. Examples of suitable paramagnetic metal ions, include, but are not limited to, gadolinium III (Gd+3 or Gd(III)), iron III (Fe+3 or Fe(III)), manganese II (Mn+2 or Mn(II)), yttrium III (Yt+3 or Yt(III)), dysprosium (Dy+3 or Dy(III)), and chromium (Cr(III) or Cr+3). In a preferred embodiment the paramagnetic ion is the lanthanide atom Gd(III), due to its high magnetic moment ($u^2$=63BM2), a symmetric electronic ground state (S8), and its current approval for diagnostic use in humans.

In addition to the metal ion, the metal ion complexes of the invention comprise a chelator. Due to the relatively high toxicity of many of the paramagnetic ions, the ions are rendered nontoxic in physiological systems by binding to a suitable chelator as outlined herein.

Accordingly, the present invention provides a number of suitable chelators for use in the present invention. The chelators shown below do not depict the chelated metal ion, although as will be appreciated by those in the art, they may be present as well.

In a preferred embodiment, the chelators have the structure depicted below:

Structure 1

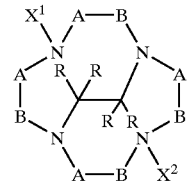

In some embodiments, the nitrogen atoms of the ring may be independently replaced with either oxygen or sulfur, depending on the metal ion; however, when the preferred Gd+3 is used, nitrogen atoms are preferred.

In a preferred embodiment, the —A—B— moiety is an alkyl moiety of C1–5, with alkyl, alkene, and alkyne bonds possible. In preferred embodiments, the —A—B— moiety is an alkyl of C2–3 selected from the group consisting of —CR$_2$—CR$_2$—, —CR=CR—, —CR$_2$—CR$_2$—CR$_2$—, —CR=CR—CR$_2$— and —CR$_2$—CR=CR— as is depicted in FIG. 2. The R substitution groups are as defined below.

The X groups of the invention (sometimes referred to herein as the "arms" of the chelator) generally provide one or more additional coordination atoms. Again, the choice of the coordination atom will depend on the metal ion used, with —COOH groups being a coordination moiety of preference with Gd+3. In some embodiments, straight alkyl chains (including both substituted alkyl, heteroalkyl and substituted heteroalkyl) are used. In alternate embodiments, the X groups depicted herein can be branched alkyl structures, with a single alkyl group comprising at least one carbon atom branching to provide multiple coordination atoms as depicted in Structure 3, below.

In general, when not attached, the X groups of the Structures are independently selected from the group consisting of —(CR$_2$)$_n$COO$^-$, —(CR$_2$)$_n$COOH, —CR(CR$_2$COO$^-$)$_2$, —CR(CR$_2$COOH)$_2$, —(CR$_2$)$_n$—CR((CR$_2$)$_m$—COOH)$_2$, —(CR$_2$)$_n$—CR((CR$_2$)$_m$—COO$^-$)$_2$, —(CR$_2$)$_n$—C(CR$_2$)$_m$—COOH)$_3$; and —C((CR$_2$)$_n$—COOH)$_3$. In this embodiment, n is an integer from 1 to 5, with 1, 2 and 3 being preferred; m is an integer from 0 to 5, with 0, 1 and 2 being preferred.

It is to be understood that the exact composition of the X groups will depend on the presence of the metal ion. That is, the hydrogen atoms of the coordination group can be present in the absence of the metal ion, but are absent in the presence of the metal ion. Thus, the structures depicted herein can be shown with the hydrogen atoms on the carboxyl group (in the absence of the metal ion) or without them (in the presence of the metal ion). Thus, preferred embodiments have the structure shown in Structure 2:

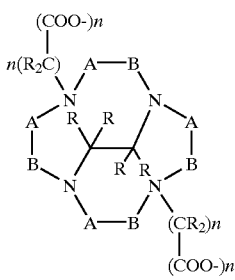

Structure 2

In this embodiment, n is an integer from one to five, with from one to three being preferred, and one and two being particularly preferred. Again, the carboxy group is shown without the hydrogen of the hydroxyl group, which will depend on the presence or absence of the metal ion.

A preferred embodiment with branching X groups is depicted in Structure 3, below:

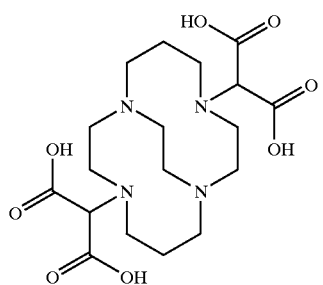

Structure 3

Structure 3 is shown with particular —A—B— groups, all R groups as hydrogen, and no metal ion.

In a preferred embodiment at least one of the R groups attached to the "arms" of the chelator (e.g. the X groups) comprises an alkyl (including substituted and heteroalkyl groups), or aryl (including substituted and heteroaryl groups), i.e. is a group sterically bulkier than hydrogen. Preferred groups include the C1 through C6 alkyl groups with methyl being particularly preferred.

However the inclusion of too many groups may drive the equilibrium in the other direction. Therefore in a preferred embodiment only 1 or 2 of these positions is a non-hydrogen group, unless other methods are used to drive the equilibrium towards binding.

In the figures and agents described herein, R is independently selected from the group consisting of hydrogen, alkyl, aryl, alcohol, amine, amido, nitro, ether, ester, ketone, imino, aldehyde, alkoxy, carbonyl, halogen, sulfur containing moiety, phosphorus containing moiety, targeting moiety, or, together with an adjacent R group forms an alkyl or aryl group.

As will be appreciated by those skilled in the art, many positions designated herein and in the structures of the figures may have more than 1 R group attached, depending on the valency of the atoms; generally, carbon atoms that are not participating in double bonds can have two R groups attached (R' and R"), although in a preferred embodiment only a single non-hydrogen R group is attached at any particular position; that is, preferably at least one of the R groups at each position is hydrogen. Thus, if R is an alkyl or aryl group, there is generally an additional hydrogen attached to the carbon, although not depicted herein. In many preferred embodiments, all the R groups are hydrogen, with the exception of targeting and blocking moieties.

By "alkyl group" or grammatical equivalents herein is meant a straight or branched chain alkyl group, with straight chain alkyl groups being preferred. If branched, it may be branched at one or more positions, and unless specified, at any position. Also included within the definition of alkyl are heteroalkyl groups, wherein the heteroatom is selected from nitrogen, oxygen, phosphorus, sulfur and silicon. Also included within the definition of an alkyl group are cycloalkyl groups such as C5 and C6 rings, and heterocycloalkyl.

Additional suitable heterocyclic substituted rings are depicted in U.S. Pat. No. 5,087,440, expressly incorporated by reference. In some embodiments, two adjacent R groups may be bonded together to form ring structures together with the carbon atoms of the chelator, such as is described in U.S. Pat. No. 5,358,704, expressly incorporated by reference. These ring structures may be similarly substituted.

The alkyl group may range from about 1 to 20 carbon atoms (C1–C20), with a preferred embodiment utilizing from about 1 to about 10 carbon atoms (C1–C10), with about C1 through about C5 being preferred. However, in some embodiments, the alkyl group may be larger, for example when the alkyl group is the coordination site barrier.

By "alkyl amine" or grammatical equivalents herein is meant an alkyl group as defined above, substituted with an amine group at any position. In addition, the alkyl amine may have other substitution groups, as outlined above for alkyl group. The amine may be primary (—NH$_2$R), secondary (—NHR$_2$), or tertiary (—NR$_3$). When the amine is a secondary or tertiary amine, suitable R groups are alkyl groups as defined above. A preferred alkyl amine is p-aminobenzyl. When the alkyl amine serves as the coordination site barrier, as described below, preferred embodiments utilize the nitrogen atom of the amine as a coordination atom, for example when the alkyl amine includes a pyridine or pyrrole ring.

By "aryl group" or grammatical equivalents herein is meant aromatic aryl rings such as phenyl, heterocyclic aromatic rings such as pyridine, furan, thiophene, pyrrole, indole and purine, and heterocyclic rings with nitrogen, oxygen, sulfur or phosphorus.

Included within the definition of "alkyl" and "aryl" are substituted alkyl and aryl groups. That is, the alkyl and aryl groups may be substituted, with one or more substitution groups. For example, a phenyl group may be a substituted phenyl group. Suitable substitution groups include, but are not limited to, halogens such as chlorine, bromine and fluorine, amines, hydroxy groups, carboxylic acids, nitro groups, carbonyl and other alkyl and aryl groups as defined herein. Thus, arylalkyl and hydroxyalkyl groups are also suitable for use in the invention. Preferred substitution groups include alkyl amines and alkyl hydroxy.

In some embodiments, adjacent R groups can be joined to form cyclic structures, either cycloalkyl, cycloheteroalkyl, aryl, heteroaryl, or pluricyclic structures comprising a combination of these ring structures, including substituted derivatives of any of these. Similarly, when the R groups are alkyl and aryl groups, pluricyclic groups including cycloalkyl, cycloheteroalkyl, aryl, heteroaryl and substituted derivatives can also be used.

By "amino groups" or grammatical equivalents herein is meant —NH$_2$, —NHR and —NR$_2$ groups, with R being as defined herein.

By "nitro group" herein is meant an —NO$_2$ group.

By "sulfur containing moieties" herein is meant compounds containing sulfur atoms, including but not limited to, thia-, thio- and sulfo- compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—(CH$_2$)$_2$CH$_3$ and —O—(CH$_2$)$_4$CH$_3$ being preferred.

By "ester" herein is meant a —COOR group.

By "halogen" herein is meant bromine, iodine, chlorine, or fluorine. Preferred substituted alkyls are partially or fully halogenated alkyls such as CF$_3$, etc.

By "aldehyde" herein is meant —RCHO groups.

By "alcohol" or "alkoxy" herein is meant —OH groups, and alkyl alcohols —ROH.

By "amido" herein is meant —RCONH— or RCONR— groups.

By "ethylene glycol" or "(poly)ethylene glycol" herein is meant a —(O—CH$_2$—CH$_2$)$_n$— group, although each carbon atom of the ethylene group may also be singly or doubly substituted, i.e. —(O—CR$_2$—CR$_2$)$_n$—, with R as described above. Ethylene glycol derivatives with other heteroatoms in place of oxygen (i.e. —(N—CH$_2$—CH$_2$)$_n$— or —(S—CH$_2$—CH$_2$)$_n$—, or with substitution groups) are also preferred.

By "ketone" herein is meant —R—CO—R—.

By "imino group" herein is meant —C—NH—C.

By "carbonyl" herein is meant —C=O.

By "phosphorous moieties" herein is meant moieties containing the —PO(OH)(R)$_2$ group. The phosphorus may be an alkyl phosphorus; for example, DOTEP utilizes ethylphosphorus as a substitution group on DOTA. R is as defined above, with preferred embodiments utilizing alkyl, substituted alkyl and hydroxy. A preferred embodiment has a —PO(OH)$_2$R group.

In addition, the complexes and metal ion complexes of the invention may further comprise one or more targeting moieties; i.e. one or more R groups may be a targeting moiety. That is, a targeting moiety may be attached at any of the R positions (or to a linker, including a polymer, or to a blocking moiety, etc.), although in a preferred embodiment the targeting moiety does not replace a coordination atom. By "targeting moiety" herein is meant a functional group which serves to target or direct the complex to a particular location, cell type, diseased tissue, or association. In general, the targeting moiety is directed against a target molecule. As will be appreciated by those in the art, the MRI contrast agents of the invention are generally injected intravenously; thus preferred targeting moieties are those that allow concentration of the agents in a particular localization. Thus, for example, antibodies, cell surface receptor ligands and hormones, lipids, sugars and dextrans, alcohols, bile acids, fatty acids, amino acids, peptides and nucleic acids may all be attached to localize or target the contrast agent to a particular site.

In a preferred embodiment, the targeting moiety allows targeting of the MRI agents of the invention to a particular tissue or the surface of a cell.

As will be appreciated by those in the art, the targeting moieties can be attached in a large number of different ways, and in a variety of configurations.

In a preferred embodiment, the targeting moiety is a peptide. For example, chemotactic peptides have been used to image tissue injury and inflammation, particularly by bacterial infection; see WO 97/14443, hereby expressly incorporated by reference in its entirety.

In a preferred embodiment, the targeting moiety is an antibody. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies.

In a preferred embodiment, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin 10 [Jones et al., Nature 321:522–525 (1986); Riechmann et al., Nature 332:323–329 (1988); and Presta, Curr. Op. Struct. Biol. 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature 321:522–525 (1986); Riechmann et al., Nature 332:323–327 (1988); Verhoeyen et al., Science 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage 25 display libraries [Hoogenboom and Winter, J. Mol. Biol. 227:381 (1991); Marks et al., J. Mol. Biol. 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol. 147(1)

:86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10:779–783 35 (1992); Lonberg et al., Nature 368:856–859 (1994); Morrison, Nature 368:812–13 (1994); Fishwild et al., Nature Biotechnology 14:845–51 (1996); Neuberger, Nature Biotechnology, 14:826 (1996); Lonberg and Huszar, Intern. Rev. Immunol. 13:65–93 (1995).

Bispecific antibodies are monoclonal, preferably human or humanized, antibodies that have binding specificities for at least two different antigens. In the present case, one of the binding specificities is for a first target molecule and the other one is for a second target molecule.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J. 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a preferred embodiment, the antibody is directed against a cell-surface marker on a cancer cell; that is, the target molecule is a cell surface molecule. As is known in the art, there are a wide variety of antibodies known to be differentially expressed on tumor cells, including, but not limited to, HER2, VEGF, etc.

In addition, antibodies against physiologically relevant carbohydrates may be used, including, but not limited to, antibodies against markers for breast cancer (CA 15–3, CA 549, CA 27.29), mucin-like carcinoma associated antigen (MCA), ovarian cancer (CA 125), pancreatic cancer (DE-PAN-2), and colorectal and pancreatic cancer (CA 19, CA 50, CA242).

In a preferred embodiment, the targeting moiety is all or a portion (e.g. a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimutating hormone, norepinephrine, parathryroid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

In a preferred embodiment, the targeting moiety is a carbohydrate. By "carbohydrate" herein is meant a compound with the general formula $Cx(H_2O)y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, mannose, fucose, galactosamine, (particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates. In particular, polysaccharides (including, but not limited to, arabinogalactan, gum arabic, mannan, etc.) have been used to deliver MRI agents into cells; see U.S. Pat. No. 5,554,386, hereby incorporated by reference in its entirety.

In a preferred embodiment, the targeting moiety is a lipid. "Lipid" as used herein includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In a preferred embodiment, the targeting moiety is selected from the group consisting of enzyme substrates or inhibitors, receptor ligands, antibodies, antigens, ion binding compounds, substantially complementary nucleic acids, nucleic acid binding proteins, etc.

In a preferred embodiment, the targeting moiety may be used to either allow the internalization of the MRI agent to the cell cytoplasm or localize it to a particular cellular compartment, such as the nucleus.

In a preferred embodiment, the targeting moiety is all or a portion of the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, the targeting moiety is a nuclear localization signal (NLS). NLSs are generally short, positively charged (basic) domains that serve to direct the moiety to which they are attached to the cell's nucleus. Numerous NLS amino acid sequences have been reported including single basic NLS's such as that of the SV40 (monkey virus) large T Antigen (Pro Lys Lys Lys Arg Lys Val), Kalderon (1984), et al., Cell, 39:499–509; the human retinoic acid receptor-β nuclear localization signal (ARRRRP); NFKB p50 (EEVQRKRQKL; Ghosh et al., Cell 62:1019 (1990); NFKB p65 (EEKRKRTYE; Nolan et al., Cell 64:961 (1991); and others (see for example Boulikas, J. Cell. Biochem. 55(1):32–58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp), Dingwall, et al., Cell, 30:449–458, 1982 and Dingwall et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, targeting moieties for the hepatobiliary system are used; see U.S. Pat. Nos. 5,573,752 and 5,582,814, both of which are hereby incorporated by reference in their entirety.

In a preferred embodiment, the metal ion complexes of the present invention are water soluble or soluble in aqueous solution. By "soluble in aqueous solution" herein is meant that the MRI agent has appreciable solubility in aqueous solution and other physiological buffers and solutions. Solubility may be measured in a variety of ways. In one embodiment, solubility is measured using the United States Pharmacopeia solubility classifications, with the metal ion complex being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute).

Testing whether a particular metal ion complex is soluble in aqueous solution is routine, as will be appreciated by those in the art. For example, the parts of solvent required to solubilize a single part of MRI agent may be measured, or solubility in gm/ml may be determined.

In a preferred embodiment, the MRI contrast agents of the invention comprise more than one metal ion, such that the signal is increased. As is outlined below, this may be done in a number of ways, including, but not limited to, the use of multiple metal ions in a single chelate, the use of a single blocking moiety to block more than one chelated metal ion, or the oligomerization of the agents of the invention, including both multimers and the use of polymeric linkers to attach agents together.

In a preferred embodiment, the MRI agents of the invention comprise at least two paramagnetic metal ions, each with a chelator; that is, multimeric MRI agents are made. In a preferred embodiment, the chelators are linked together, either directly or through the use of a linker such as a coupling moiety or polymer. For example, using substitution groups that serve as functional groups for chemical attachment on the chelator, attachment to other chelators may be accomplished.

In a preferred embodiment, the chelators of the invention include one or more substitution groups that serve as functional groups for chemical attachment. Suitable functional groups include, but are not limited to, amines (preferably primary amines), carboxy groups, and thiols (including SPDP, alkyl and aryl halides, maleimides, α-haloacetyls, and pyridyl disulfides) are useful as functional groups that can allow attachment.

In one embodiment, the chelators are linked together directly, using at least one functional group on each chelator. This may be accomplished using any number of stable bifunctional groups well known in the art, including homobifunctional and heterobifunctional linkers (see Pierce Catalog and Handbook, 1994, pages T155–T200, hereby expressly incorporated by reference). This may result in direct linkage, for example when one chelator comprises a primary amine as a functional group and the second comprises a carboxy group as the functional group, and carbodiimide is used as an agent to activate the carboxy for attach by the nucleophilic amine (see Torchilin et al., *Critical Rev. Therapeutic Drug Carrier Systems*, 7(4):275–308 (1991). Alternatively, as will be appreciated by those in the art, the use of some bifunctional linkers results in a short coupling moiety being present in the structure. A "coupling moiety" is capable of covalently linking two or more entities. In this embodiment, one end or part of the coupling moiety is attached to the first MRI contrast agent, and the other is attached to the second MRI agent. The functional group(s) of the coupling moiety are generally attached to additional atoms, such as alkyl or aryl groups (including hetero alkyl and aryl, and substituted derivatives), to form the coupling moiety. Oxo linkers are also preferred. As will be appreciated by those in the art, a wide range of coupling moieties are possible, and are generally only limited by the ability to synthesize the molecule and the reactivity of the functional group. Generally, the coupling moiety comprises at least one carbon atom, due to synthetic requirements; however, in some embodiments, the coupling moiety may comprise just the functional group.

In a preferred embodiment, the coupling moiety comprises additional atoms as a spacer. As will be appreciated by those in the art, a wide variety of groups may be used. For example, a coupling moiety may comprise an alkyl or aryl group substituted with one or more functional groups. Thus, in one embodiment, a coupling moiety containing a multiplicity of functional groups for attachment of multiple MRI contrast agents may be used, similar to the polymer embodiment described below. For example, branched alkyl groups containing multiple functional groups may be desirable in some embodiments.

In an additional embodiment, the linker is a polymer. In this embodiment, a polymer comprising at least one MRI contrast agent of the invention is used. Preferred embodiments utilize a plurality of MRI agents per polymer. The number of MRI agents per polymer will depend on the density of MRI agents per unit length and the length of the polymer.

The character of the polymer will vary, but what is important is that the polymer either contain or can be modified to contain functional groups for the the attachment of the MRI contrast agents of the invention. Suitable polymers include, but are not limited to, functionalized dextrans, styrene polymers, polyethylene and derivatives, polyanions including, but not limited to, polymers of heparin, polygalacturonic acid, mucin, nucleic acids and their analogs including those with modified ribose-phosphate backbones, the polypeptides polyglutamate and polyaspartate, as well as carboxylic acid, phosphoric acid, and sulfonic acid derivatives of synthetic polymers; and polycations, including but not limited to, synthetic polycations based on acrylamide and 2-acrylamido-2-methylpropanetrimethylamine, poly(N-ethyl-4-vinylpyridine) or similar quaternized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, spermine, spermidine and polypeptides such as protamine, the histone polypeptides, polylysine, polyarginine and polyornithine; and mixtures and derivatives of these. Particularly preferred polycations are polylysine and spermidine, with the former being especially preferred. Both optical isomers of polylysine can be used. The D isomer has the advantage of having long-term resistance to cellular proteases. The L isomer has the advantage of being more rapidly cleared from the subject. As will be appreciated by those in the art, linear and branched polymers may be used.

A preferred polymer is polylysine, as the —NH$_2$ groups of the lysine side chains at high pH serve as strong nucleophiles for multiple attachment of activated chelating agents. At high pH the lysine monomers are coupled to the MRI agents under conditions that yield on average 5–20% monomer substitution.

In some embodiments, particularly when charged polymers are used, there may be a second polymer of opposite charge to the first that is electrostatically associated with the first polymer, to reduce the overall charge of polymer-MRI agent complex. This second polymer may or may not contain MRI agents.

The size of the polymer may vary substantially. For example, it is known that some nucleic acid vectors can deliver genes up to 100 kilobases in length, and artificial chromosomes (megabases) have been delivered to yeast. Therefore, there is no general size limit to the polymer. However, a preferred size for the polymer is from about 10 to about 50,000 monomer units, with from about 2000 to about 5000 being particularly preferred, and from about 3 to about 25 being especially preferred.

It should be understood that the multimeric MRI agents of the invention may be made in a variety of ways, including those listed above. What is important is that manner of attachment does not significantly alter the functionality of the agents.

As outlined above, the MRI agents may also be combined into higher multimers, either by direct linkage or via attachment to a polymer.

The complexes of the invention are generally synthesized using well known techniques and as outlined in the Examples.

The contrast agents of the invention are complexed with the appropriate metal ion as is known in the art. While the structures depicted herein all comprise a metal ion, it is to be understood that the contrast agents of the invention need not have a metal ion present initially. Metal ions can be added to water in the form of an oxide or in the form of a halide and treated with an equimolar amount of a contrast agent composition. The contrast agent may be added as an aqueous solution or suspension. Dilute acid or base can be added if need to maintain a neutral pH. Heating at temperatures as high as 100° C. may be required.

The complexes of the invention can be isolated and purified, for example using HPLC systems.

Pharmaceutical compositions comprising pharmaceutically acceptable salts of the contrast agents can also be prepared by using a base to neutralize the complexes while they are still in solution. Some of the complexes are formally uncharged and do not need counterions.

Once synthesized, the metal ion complexes of the invention have use as magnetic resonance imaging contrast or enhancement agents.

The metal ion complexes of the invention may be used in a similar manner to the known gadolinium MRI agents. See for example, Meyer et al., supra; U.S. Pat. Nos. 5,155,215; 5,087,440; Margerstadt et al., Magn. Reson. Med. 3:808 (1986); Runge et al., Radiology 166:835 (1988); and Bousquet et al., Radiology 166:693 (1988). The metal ion complexes are administered to a cell, tissue or patient as is known in the art. A "patient" for the purposes of the present invention includes both humans and other animals and organisms, such as experimental animals. Thus the methods are applicable to both human therapy and veterinary applications. In addition, the metal ion complexes of the invention may be used to image tissues or cells; for example, see Aguayo et al., Nature 322:190 (1986).

Generally, sterile aqueous solutions of the contrast agent complexes of the invention are administered to a patient in a variety of ways, including orally, intrathecally and especially intraveneously in concentrations of 0.003 to 1.0 molar, with dosages from 0.03, 0.05, 0.1, 0.2, and 0.3 millimoles per kilogram of body weight being preferred. Dosages may depend on the structures to be imaged. Suitable dosage levels for similar complexes are outlined in U.S. Pat. Nos. 4,885,363 and 5,358,704.

In addition, the contrast agents of the invention may be delivered via specialized delivery systems, for example, within liposomes (see Navon, Magn. Reson. Med. 3:876–880 (1986)) or microspheres, which may be selectively taken up by different organs (see U.S. Pat. No. 5,155,215).

In some embodiments, it may be desirable to increase the blood clearance times (or half-life) of the MRI agents of the invention. This has been done, for example, by adding carbohydrate polymers to the chelator (see U.S. Pat. No. 5,155,215). Thus, one embodiment utilizes polysaccharides as substitution R groups on the compositions of the invention.

A preferred embodiment utilizes complexes which cross the blood-brain barrier. Thus, as is known in the art, a DOTA derivative which has one of the carboxylic acids replaced by an alcohol to form a neutral DOTA derivative has been shown to cross the blood-brain barrier. Thus, for example, neutral complexes are designed that cross the blood-brain barrier with blocking moieties which detect Ca+2 ions. These compounds are used in MRI of a variety of neurological disorders, including Alzeheimer's disease. Currently it is difficult to correctly diagnosis Alzeheimer's disease, and it would be useful to be able to have a physiological basis to distinguish Alzeheimer's disease from depression, or other treatable clinical symptoms for example.

All references cited herein are incorporated by reference.

EXAMPLES

Below are given the reaction sequence for the cyclam (14aneN4) macrocyle. The same reaction sequence works identically for cyclen (14aneN4) and homocyclen (13aneN4). FIG. 3 depicts the synthetic scheme.

Diacetic Acid Bridged Cyclam:

In a 1 L roundbottom flask, 0.032 mol (7.248 g) $H_2$ Bcyclam, synthesized according to reference 2, was stirred with 500 ml dry acetonitrile. Potassium carbonate, 35 g, was added and the vessel was placed under argon. Ethyl iodoacetate (2 eg., 13.70 g, 7.6 ml) was added and the reaction mixture stirred at room temperature for 3.5 h under argon. Upon reaction completion, the reaction mixture was filtered to remove $K_2CO_3$ and rotovapped to a solid. Mass Spec, and NMR characterization at this point were consistent with the diester. The ester groups were hydrolyzed to the acids at this point. The solid was dissolved in 400 ml 50% ethanol/water and stirred overnight with 300 ml IRA-400(OH.) anion exchange resin. [The resin had been prepared by washing with 2×500 ml 2 M NaOH, then 500 ml water to remove excess OH⁻.] Filtration followed by solvent evaporation yielded 6.64 g (61%) of the product as a yellow viscous oil. Mass and NMR spectra were obtained in $D_2O$ and were consistent with the product.

Mn(AcBcyclam) and Mn(AcBcyclam)$PF_6$ (Same for $Fe^{2+/3+}$):

The AcBcyclam ligand (0.001 mol, 0.342 g) was suspended in 25 ml 4:1 acetonitrile:methanol solution in a 2-neck 100 ml roundbottom flask. A solid addition funnel was loaded with $MnCl_2$ (0.001 mol, 0.126 g) and attached to the reaction flask. The solution was rigorously degassed by flushing it with argon then putting it under vacuum with the solvent boiled. This procedure was repeated four times. The reaction vessel was left under argon and the $MnCl_2$ was added from the funnel. The pink $MnCl_2$ dissolved quickly giving a gray suspension. The reaction was stirred at reflux for 1.5 h using a water bath (70° C.). The reaction was then cooled in an ice bath to complete the precipitation, and the white suspended solid filtered on a fine glass frit. This solid was likely excess $MnCl_2$. The pale green filtrate was evaporated to a pale orange sticky solid crude product. X-ray quality colorless crystals were grown from ether diffusion into a MeCN/MeOH solution. The complex in solution was air sensitive and grew more colored with time. Bulk recrystallization therefore did not yield pure product. ESMS⁺ gave large peaks at 396=MnL, and 434=MnLK.

Due to the air sensitivity of the product, it was oxidized to a more stable Mn(III) form as follows. 5 eq 30 $NH_4PF_6$ and the crude Mn(II) complex (6.32×10⁻⁴ mol, 250 mg) were dissolved in 12 ml MeOH. Argon was bubbled through the solution for 5 minutes. Molecular bromine (5 drops) was added to the reaction mixture causing an instant precipitation of an orange solid. Argon was again bubbled through the reaction (15 min) to remove excess $Br_2$. The reaction was cooled at 4° C. overnight to complete precipitation. The product was then collected on a fine glass frit and washed with MeOH and ether. The yield was 283 mg. ESMS⁺ gave a large peak at 395=MnL. Elemental analysis calc for MnLPF$_6$.NH$_4$PF$_6$.MeOH: C 27.77, H 4.93, N 9.52. Found: C 27.93, H 4.41, N 907.

Gd(AcBcyclam)Cl and Gd(AcBcyclam)PF$_6$:

The ligand AcBcyclam (0.001 mol, 0.342 g) was dissolved in 15 dry DMF and placed under argon. To this stirring solution was added $GdCl_3$ (0.001 mol, 0.264 g) as a solid. The reaction mixture was heated to reflux under argon overnight. A white suspended solid was present in the reaction mixture. Attempts at filtration of this material (KCl?) were unsuccessful, so all materials were recombined by redissolving any solid with MeOH. The combined DMF/MeOH solution was evaporated to an off-white solid. Electrospray mass spec. gave peaks at 534=GdLCl and 572= KGdLCl. Ether diffusion into a methanol solution gave colorless crystals whose X-ray structure has been determined and matches that given below. Elemental analysis: calc GdLCl.KCl.4H$_2$O: C 27.54, H 5.49, N 8.03; found C 27.70, H 4.87, N 8.20. The relaxivity of the chloride complex was measured at 22° C. at 500 Mgz, at pH 5.5 and was found to be 7.5 mM⁻¹s⁻¹, roughly twice that of currently clinically used contrast agents.

We claim:

1. A chelating agent comprising a compound having the formula:

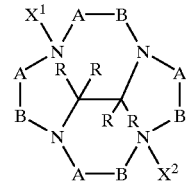

wherein

A—B is a structure selected from the group consisting of —$CR_2$—$CR_2$—, —CR=CR—, —$CR_2$—$CR_2$—$CR_2$—, CR=CR—$CR_2$— and —$CR_2$—CR=CR, and wherein at least one A—B structure is —CR=CR—;

$X^1$ and $X^2$ are independently selected from the group consisting of $CR_2COOH$, and $CR(CR_2COOH)_2$;

each R is independently selected from the group consisting of hydrogen, alkyl, aryl, alcohol, amine, amido, nitro, ether, ester, ketone, imino, aldehyde, alkoxy, carbonyl, halogen, sulfur containing moiety, phosphorus containing moiety, targeting moiety, or, together with an adjacent R group forms an alkyl or aryl group; or a salt thereof.

2. An MRI composition comprising a compound having the formula:

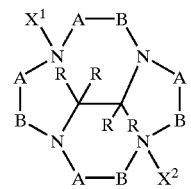

wherein

A—B is a structure selected from the group consisting of —$CR_2$—$CR_2$—, —CR=CR—, —$CR_2$—$CR_2$—

$CR_2$—, CR=CR—$CR_2$— and —$CR_2$—CR=CR, and wherein at least one A—B structure is —CR=CR—;

$X^1$ and $X^2$ are independently selected from the group consisting of $CR_2$ $COO^-$, and $CR(CR_2COO^-)_2$;

each R is independently selected from the group consisting of hydrogen, alkyl, aryl, alcohol, amine, amido, nitro, ether, ester, ketone, imino, aldehyde, alkoxy, carbonyl, halogen, sulfur containing moiety, phosphorus containing moiety, targeting moiety, or, together with an adjacent R group forms an alkyl or aryl group; and a paramagnetic ion; or a salt thereof.

3. An MRI composition according to claim 2 wherein said paramagnetic ion is Gd+3.

4. An MRI composition comprising a compound having a formula:

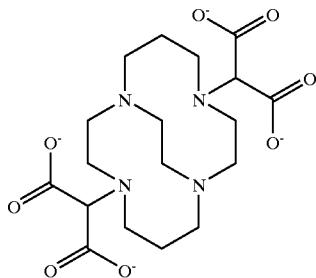

wherein a hydrogen is attached at all positions capable of having one or more R groups attached; and a paramagnetic ion; or a salt thereof.

5. A method of magnetic resonance imaging of a cell, tissue or patient comprising administering an MRI agent according to claim 2 to a cell, tissue or patient and rendering a magnetic resonance image of said cell, tissue or patient.

6. An MRI composition according to claim 2, wherein $X^1$ and $X^2$ are $CH(COO^-)_2$.

7. An MRI composition according to claim 2, wherein $X^1$ or $X^2$ are independently selected from the group consisting of $CR_2$ $COO^-$, $CR(CR_2COO^{31})_2$; and, at least one R group is a targeting moiety.

8. An MRI composition according to claim 7, further comprising a polymer.

9. An MRI composition according to claim 4, further comprising a polymer.

10. An MRI composition according to claim 4, wherein said paramagnetic ion is Gd+3.

* * * * *